United States Patent [19]
Albright, Jr.

[11] Patent Number: 5,130,490
[45] Date of Patent: Jul. 14, 1992

[54] PURIFICATION OF 3,5-DIAMINOBENZOTRIFLUORIDE BY SELECTIVE PRECIPITATION OF THE HYDROCHLORIDE SALT

[75] Inventor: David E. Albright, Jr., Niagara Falls, N.Y.

[73] Assignee: Occidental Chemical Corporation, Niagara Falls, N.Y.

[21] Appl. No.: 797,582

[22] Filed: Nov. 25, 1991

[51] Int. Cl.$^5$ ............................................. C07C 209/86
[52] U.S. Cl. ................................................. 564/438
[58] Field of Search ........................................ 564/438

[56] References Cited

U.S. PATENT DOCUMENTS 3,452,096  6/1969  Palevada et al. ............... 564/425 X
3,452,097  6/1969  Beale et al. .................... 564/498 X
4,409,386  10/1983  Chang ............................ 564/438
4,532,352  7/1985  Patton ............................ 564/438

FOREIGN PATENT DOCUMENTS 1270855  6/1990  Canada .
0061552  4/1985  Japan .

Primary Examiner—Richard L. Raymond
Attorney, Agent, or Firm—James F. Tao; Richard D. Fuerle

[57] ABSTRACT

3,5-Diaminobenzotrifluoride can be readily separated from 4-chloro-3,5-diaminobenzotrifluoride by the addition of hydrogen chloride. 3,5-Diaminobenzotrifluoride forms hydrochloride salt, while 4-chloro-3,5-diaminobenzotrifluoride does so much less readily.

15 Claims, No Drawings

PURIFICATION OF 3,5-DIAMINOBENZOTRIFLUORIDE BY SELECTIVE PRECIPITATION OF THE HYDROCHLORIDE SALT

BACKGROUND OF THE INVENTION 3,5-Diaminobenzotrifluoride is useful as a monomer for the production of polyimide resins. As produced, the product often occurs with several percent of 4-chloro-3,5-diaminobenzotrifluoride as an impurity. The diamine and the chloro-diamine have similar boiling points and are, therefore, difficult to separate by distillation. They have similar crystallization properties and are, therefore, difficult to separate by recrystallization.

Canadian Patent 1,270,855 discloses a process for separating a para-fluoroaniline from the corresponding non-fluorine substituted aniline. Thus, for example, para-fluoroaniline can be separated from aniline and para-fluoro-meta-chloroaniline can be separated from meta-chloroaniline. The process involves dissolving the anilines in an aqueous solution of a non-oxidizing acid such as hydrochloric acid, and fractionally crystallizing the hydrochloride salts. The para-fluoroaniline crystallizes in preference to the non-fluorinated aniline, and accordingly, the crystalline product produced is enriched in the para-fluoro compound. Depending on the degree of purity desired, several recrystallizations may be required. Further quantities of the para-fluoroaniline can be recovered from the mother liquor, since upon evaporation, the para-fluoro aniline will crystallize in preference to the unfluorinated aniline.

U.S. Pat. No. 3,452,096 discloses a method for separating 2,3-dichloroaniline from 2,5-dichloroaniline and 3,4-dichloroaniline. The method involves treating a mixture of dichloroaniline with either a monovalent inorganic acid or with an aroylhalide to produce either the acid addition salt of 2,3-dichloroaniline or the n-acyl derivative of 2,3-dichloroaniline. The acid salt or the n-acyl derivatives of 2,3-dichloroaniline are less soluble than those of the other isomers and, therefore, precipitate preferentially.

U.S. Pat. No. 4,532,352 discloses a process for the separation of para-fluoroaniline from a mixture containing aniline and para-fluoroaniline. The process comprises contacting the mixture with a mineral acid in the presence of an organic solvent and separating the insoluble hydrochloride salt of para-fluoroaniline by conventional means such as filtration. If desired, the isolated salt can be converted to para-fluoroaniline by reaction with a base.

SUMMARY OF THE INVENTION

Surprisingly, it has now been discovered that 3,5-diaminobenzotrifluoride can be readily separated from 4-chloro-3,5-diaminobenzotrifluoride by the addition of hydrogen chloride. 3,5-Diaminobenzotrifluoride forms a hydrochloride salt, while 4-chloro-3,5-diaminobenzotrifluoride does so much less readily.

DETAILED DESCRIPTION OF THE INVENTION

Surprisingly, it has been found that when a mixture of 3,5-diaminobenzotrifluoride (DABTF) and 4-chloro-3,5-diaminobenzotrifluoride (CDABTF) is exposed to a source of hydrogen chloride, the 3,5-diaminobenzotrifluoride readily forms a hydrochloride salt, while the 4-chloro-3,5-diaminobenzotrifluoride much less readily does so. When up to two equivalents of hydrogen chloride are added, the HCl reacts entirely with the 3,5-diaminobenzotrifluoride in preference to the 4-chloro-3,5-diaminobenzotrifluoride.

The mixture of 4-chloro-3,5-diaminobenzotrifluoride and 3,5-diaminobenzotrifluoride can be exposed to hydrogen chloride in many different ways, provided that no more than 2 moles of hydrogen chloride for each mole of 3,5-diaminobenzotrifluoride are taken up in the reaction. Each method produces the same result, that is, the 3,5-diaminobenzotrifluoride produces a hydrochloride salt and the 4-chloro derivative does not. Accordingly, after the mixture has been brought into contact with a source of hydrogen chloride, the separation of the two compounds can be readily accomplished since the 3,5-diaminobenzotrifluoride now exists as the hydrochloride salt whereas the 4-chloro-3,5-diaminobenzotrifluoride exists as the amine. The difference in solubility between the amine and the hydrochloride salt of an amine may be readily exploited to achieve the desired separation.

There are several methods by which the hydrochloride salt can be separated from the non-reactive amine. One method is to dissolve the mixture of 3,5-diaminobenzotrifluoride and 4-chloro-3,5-diaminobenzotrifluoride in an organic solvent which is stable to acid. The solution can then be exposed to an aqueous solution of hydrochloric acid. The 3,5-diaminobenzotrifluoride forms the hydrochloride salt, which is soluble in the aqueous phase. If a sufficient quantity of the aqueous solution of hydrochloric acid is used, all of the 3,5-diaminobenzotrifluoride will dissolve in the aqueous phase from which it can be recovered by techniques well known to those skilled in the art. If a smaller quantity of aqueous hydrochloric acid is used, not all of the hydrochloride salt will be able to dissolve in the aqueous phase, and some will precipitate out from the organic phase from which it may be collected. In any case, the 4-chloro-3,5-diaminobenzotrifluoride remains unreacted and stays in the organic phase. Ethyl acetate is a good solvent for this process. When the process is conducted on a larger scale, care must be taken to minimize the hydrolysis of the ethyl acetate. When ethyl acetate is used as the solvent, and the solution is exposed to aqueous hydrochloric acid, the hydrochloride salt precipitates out of solution and is recovered by filtration or other means well known to those skilled in the art. The aqueous phase contains additional quantities of the hydrochloride salt, while the 4-chloro-3,5-diaminobenzotrifluoride remains in the ethyl acetate phase. The aqueous phase and the organic phase can be readily separated by methods known to those skilled in the art.

Another method of practicing the invention is to dissolve the mixture of 4-chloro-3,5-diaminobenzotrifluoride and 3,5-diaminobenzotrifluoride in an organic solvent which is stable to acid. Anhydrous hydrogen chloride gas is introduced into this solution and the hydrochloride salt of 3,5-diaminobenzotrifluoride precipitates from the organic phase while 4-chloro-3,5-diaminobenzotrifluoride remains in the organic solution. In practice, excess hydrogen chloride can be bubbled through the solution. However, care must be taken to assure that no more than 2 moles of hydrogen chloride per mole of 3,5-diaminobenzotrifluoride are absorbed. As an example of a process of this sort, the mixture of amines can be dissolved in ethyl acetate. Hydrogen gas bubbled through the mixture is rapidly taken up by the amine, and the 3,5-diaminobenzotrifluoride hydrochloride quickly precipitates from the solution. The 4-chloro-3,5-diaminobenzotrifluoride remains in the ethyl acetate. A wide variety of organic solvents are suitable for use in this invention. One requirement for a solvent is that it have minimal interaction with hydrogen chloride. Amine solvents are not suitable because they react with hydrogen chloride. Similarly, carboxylic acid solvents are not suitable because they tend to react with the diamine. Dipolar aprotic solvents, and polar solvents such as alcohol can be used. However, the hydrochloride salt has appreciable solubility in such solvents, and partial solvent evaporation may be required to recover the amine hydrochloride. Hydrocarbon solvents, such as toluene or xylene, can be used. In these solvents, the hydrochloride salt tends to crystallize very rapidly, and the crystals are small and poorly formed. As a result, the precipitate of the hydrochloride salt from solvents such as toluene may be difficult to handle. Low molecular weight esters such as ethyl acetate are the preferred solvents for this separation process. Although the esters are subject to hydrolysis under acid conditions, the process can be conducted at moderate temperatures, and quickly enough so that hydrolysis is minimal. The hydrochloride salt precipitates out of the ester solvents in small but easy to handle crystals.

In yet another method of practicing the invention, the mixture of 3,5-diaminobenzotrifluoride and 4-chloro-3,5-diaminobenzotrifluoride can be melted and the molten organic material contacted with aqueous hydrochloric acid. Since the diaminobenzotrifluoride itself melts around 90°, the process can be conveniently conducted by exposing the mixture of amines to a refluxing aqueous hydrochloric acid solution. After a suitable period of contact, the remaining organic phase is separated from the aqueous phase. At the elevated temperature, the hydrochloride salt of 3,5-diaminobenzotrifluoride is entirely soluble in the aqueous phase and upon cooling crystallizes from the solution.

The present invention is not limited to the methods exemplified above. The important feature of the invention is that the mixture of 3,5-diaminobenzotrifluoride and 4-chloro-3,5-diaminobenzotrifluoride be brought into contact with the source of hydrogen chloride whereby the hydrochloride salt of 3,5-diaminobenzotrifluoride is formed. The hydrochloride salt can be readily separated from the 4-chloro-3,5-diaminobenzotrifluoride, which does not form a salt. Equivalent methods of contacting the mixture of 3,5-diaminobenzotrifluoride and 4-chloro-3,5-diaminobenzotrifluoride with a source of hydrogen chloride, and separating the hydrochloride salt of 3,5-diaminobenzotrifluoride from the unreacted 4-chloro-3,5-diaminobenzotrifluoride, will be readily apparent to those skilled in the art.

Once the hydrochloride salt has been formed, and isolated, it can be reconverted to the amine by treatment with an inorganic base. Among the suitable inorganic bases are alkali metal and alkaline earth hydroxides, carbonates, and bicarbonates.

When the invention is used in a process that involves treatment of the mixture with an aqueous solution of hydrochloric acid, some quantity of the hydrochloride salt may remain in the water solution after the hydrochloride salt has been crystallized. The residual hydrochloride salt remaining in the aqueous phase can be recovered by partially evaporating the aqueous phase, until further quantities of the hydrochloride salt precipitate out. Alternatively, the aqueous solution can be made basic, with an inorganic base such as those listed above, thereby freeing the amine from the hydrochloride salt. The 3,5-diaminobenzotrifluoride can then be recovered by solvent extraction with an organic solvent from which it can be recovered by methods well known to those skilled in the art.

The following examples are provided to further illustrate this invention and the manner in which it can be carried out. However, it will be understood that the specific details of the examples are not to be construed as limitations on the invention.

EXAMPLES

Example 1

A solution containing 4.7 g of 3,5-diaminobenzotrifluoride (DABTF) and 0.17 g of 4-chloro-3,5-diaminobenzotrifluoride (CDABTF) in 50 ml of ethyl acetate was prepared. One equivalent (based on the DABTF) of concentrated aqueous HCl was added to the ethyl acetate solution. A white hydrochloride salt rapidly precipitated. The precipitated hydrochloride salt was recovered by filtration. The ethyl acetate filtrate was then analyzed by GC internal standard to determine the amounts of DABTF and CDABTF remaining in solution. The ethyl acetate contained only 0.06 g of DABTF (99% DABTF removal) while still containing 0.17 g of CDABTF (no loss within experimental error). The recovered hydrochloride salt was then dissolved in 40 ml of water. Excess sodium carbonate solution was added to liberate the free amine. The amine was then extracted from the aqueous phase with ethyl acetate. GC internal standard analysis of the recovered amine showed 4.6 g of pure DABTF (98 percent recovery) with no CDABTF contamination.

Example 2

A solution containing 4.7 g of DABTF and 0.17 g of CDABTF in 50 ml of ethyl acetate was prepared. Two equivalents (based on the DABTF) of concentrated aqueous HCl were added to the ethyl acetate solution. A white hydrochloride salt rapidly precipitated. The precipitated hydrochloride salt was recovered by filtration. The ethyl acetate filtrate was then analyzed by GC internal standard to determine the amounts of DABTF and CDABTF remaining in solution. The ethyl acetate contained no DABTF (100% DABTF removal) while still containing 0.16 g of CDABTF (no loss within experimental error). The recovered hydrochloride salt was then dissolved in 40 ml of water. Excess sodium carbonate solution was added to liberate the free amine. The amine was then extracted from the aqueous phase with ethyl acetate. GC internal standard analysis of the recovered amine showed 4.7 g of pure DABTF (100 percent recovery) with no CDABTF contamination.

Example 3

Approximately 1 g of DABTF and 0.9 g of CDABTF were completely dissolved in about 50 ml of ethyl acetate. Three equivalents (based on DABTF) of anhydrous HCl wa bubbled through the solution. Unreacted HCl escaped from the solution and only two equivalents actually reacted with the amine. A white precipitate rapidly formed. The precipitate was recovered by filtration and washed in ethyl acetate with the washings added to the filtrate. GC internal standard analysis of the filtrate showed it to contain 0.8 g CDABTF (essentially no CDABTF loss within experimental error) while containing only a trace of DABTF. A portion of the filter cake was completely dissolved in water. Excess potassium carbonate was added and the organic products were extracted into ethyl acetate. GC analysis of the organic layer showed pure DABTF with no CDABTF detected. Thus, nearly all of the DABTF was precipitated as DABTF hydrochloride while little or no CDABTF precipitated from the ethyl acetate solution.

I claim:

1. A process for separating 3,5-diaminobenzotrifluoride as its hydrochloride salt from a mixture containing 3,5-diaminobenzotrifluoride and 4-chloro-3,5-diaminobenzotrifluoride, which comprises the steps of
   (1) contacting said mixture with up to two moles of hydrogen chloride for each mole of 3,5-diaminobenzotrifluoride in said mixture, whereby the hydrochloride salt of 3,5-diaminobenzotrifluoride is formed, and
   (2) separating said hydrochloride salt from said 4-chloro-3,5-diaminobenzotrifluoride.

2. A process according to claim 1 with the additional step of treating the hydrochloride salt of 3,5-diaminobenzotrifluoride with an inorganic base to form 3,5-diaminobenzotrifluoride.

3. A process according to claim 1 in which the mixture of 3,5-diaminobenzotrifluoride and 4-chloro-3,5-diaminobenzotrifluoride is dissolved in an organic solvent, and an aqueous solution of hydrochloric acid is the source of said hydrogen chloride.

4. A process according to claim 3 with the additional step of treating the hydrochloride salt of 3,5-diaminobenzotrifluoride with an inorganic base to form 3,5-diaminobenzotrifluoride.

5. A process according to claim 1 in which the mixture of 3,5-diaminobenzotrifluoride and 4-chloro-3,5-diaminobenzotrifluoride is dissolved in an organic solvent, and the source of hydrogen chloride is anhydrous hydrogen chloride gas.

6. A process according to claim 5 with the additional step of treating the hydrochloride salt of 3,5-diaminobenzotrifluoride with an inorganic base to form 3,5-diaminobenzotrifluoride.

7. A process according to claim 1 in which the mixture of 3,5-diaminobenzotrifluoride and 4-chloro-3,5-diaminobenzotrifluoride is melted and the source of hydrogen chloride is an aqueous solution of hydrochloric acid.

8. A process according to claim 7 with the additional step of treating the hydrochloride salt of 3,5-diaminobenzotrifluoride with an inorganic base to form 3,5-diaminobenzotrifluoride.

9. A method of separating 3,5-diaminobenzotrifluoride from 4-chloro-3,5-diaminobenzotrifluoride in a solution in an organic solvent comprising
   (1) contacting said solution with an aqueous solution containing up to two moles of hydrogen chloride for each mole of 3,5-diaminobenzotrifluoride in said organic solvent, whereby the hydrochloride salt of 3,5-diaminobenzotrifluoride is formed, and
   (2) separating said hydrochloride salt from said organic solvent.

10. A method according to claim 9 wherein said hydrochloride salt dissolves in said aqueous solution and said aqueous solution is separated from said organic solvent.

11. A method according to claim 10 including the additional last steps of treating said hydrochloride salt with an inorganic base to form 3,5-diaminobenzotrifluoride, and separating said 3,5-diaminobenzotrifluoride from said aqueous solution.

12. A method according to claim 9 wherein said organic solvent is ethyl acetate.

13. A method of separating 3,5-diaminobenzotrifluoride from 4-chloro-3,5-diaminobenzotrifluoride in a solution of an organic solvent comprising
   (1) contacting said solution with up to two moles of hydrogen chloride gas for each mole of 3,5-diaminobenzotrifluoride in said solution, whereby the hydrochloride salt of 3,5-diaminobenzotrifluoride precipitates, and
   (2) separating said precipitate from said solution.

14. A method according to claim 13 including the additional step of treating said hydrochloride salt of 3,5-diaminobenzotrifluoride with an inorganic base to form 3,5-diaminobenzotrifluoride.

15. A method according to claim 13 wherein said organic solvent is ethyl acetate.

* * * * *